United States Patent [19]

Skatrud et al.

[11] Patent Number: 5,958,730
[45] Date of Patent: Sep. 28, 1999

[54] STREPTOCOCCUS PNEUMONIAE GENE SEQUENCE FTSY

[75] Inventors: Paul Luther Skatrud, Greenwood; Robert Brown Peery, Brownsburg; Q May Wang, Indianapolis; Paul Robert Rosteck, Jr., Indianapolis; Michele Louise Young Bellido, Indianapolis, all of Ind.

[73] Assignee: Eli Lilly and Company, Indianapolis, Ind.

[21] Appl. No.: 08/986,963

[22] Filed: Dec. 8, 1997

Related U.S. Application Data

[60] Provisional application No. 60/036,281, Dec. 13, 1996, abandoned.

[51] Int. Cl.$^6$ .............................. C12P 21/06; C12N 1/20; C12N 15/00; C07H 21/044
[52] U.S. Cl. .................. 435/69.1; 435/320.1; 435/252.3; 435/471; 536/23.7
[58] Field of Search ........................ 536/23.7; 435/320.1, 435/71.1, 69.1, 252.3, 471

[56] References Cited

PUBLICATIONS

Adrian Zelazny, et al. "The NG domain of the prokaryotic signal recognition particle receptor, FtsY, is fully functional when fused to an unrelated integral membrane polypeptide" *Proc. Natl. Acad. Sci.* 94:6025–6029 (Jun. 1997).

Ted Powers and Peter Walter. "Reciprocal Stimulation of GTP Hyrdolysis by Two Directly Interacting GTPases" *Science* 269:1422–1424 (Sep. 8, 1995).

Douglas M. Freymann, et al. "Structure of the conserved GTPase domain of the signal recognition particle" *Nature* 385:361–364 (Jan. 23, 1997).

Guillermo Montoya, et al. "Crystal structure of the NG domain from the signal–recognition particle receptor FtsY" *Nature* 385:365–368 (Jan. 23, 1997).

Nancy D. Ulbrandt, et al. "The *E. Coli* Signal Recognition Particle Is Required for the Insertion of a Subset of Inner Membrane Proteins" *Cell* 88:187–196 (Jan. 24, 1997).

*Primary Examiner*—Robert A. Wax
*Assistant Examiner*—Devesh Srivastava
*Attorney, Agent, or Firm*—Thomas D. Webster

[57] ABSTRACT

The invention provides isolated nucleic acid compounds encoding FtsY of *Streptococcus pneumoniae*. Also provided are vectors and transformed host cells for expressing the encoded protein, and a method for identifying compounds that bind and/or inhibit said protein.

13 Claims, No Drawings

STREPTOCOCCUS PNEUMONIAE GENE SEQUENCE FTSY

This application claims the benefit of U.S. Provisional Application No. 60/036,281, filed Dec. 13, 1996, now abandoned.

BACKGROUND OF THE INVENTION

This invention provides isolated DNA sequences, proteins encoded thereby, and methods of using said DNA and protein in a variety of applications.

Widespread antibiotic resistance in common pathogenic bacterial species has justifiably alarmed the medical and research communities. Frequently, resistant organisms are co-resistant to several antibacterial agents. Penicillin resistance in *Streptococcus pneumoniae* has been particularly problematic. This organism causes upper respiratory tract infections. Modification of a penicillin-binding protein (PBP) underlies resistance to penicillin in the majority of cases. Combating resistance to antibiotic agents will require research into the molecular biology of pathogenic organisms. The goal of such research will be to identify new antibacterial agents.

While researchers continue to develop antibiotics effective against a number of microorganisms, *Streptococcus pneumoniae* has been more refractory. In part, this is because *Streptococcus pneumoniae* is highly recombinogenic and readily takes up exogenous DNA from its surroundings. Thus, there is a need for new antibacterial compounds and new targets for antibacterial therapy in *Streptococcus pneumoniae*.

BRIEF SUMMARY OF THE INVENTION

The present invention relates to an isolated gene and encoded protein from *S. pneumoniae*. The invention enables: (1) preparation of probes and primers for use in hybridizations and PCR amplifications, (2) production of proteins and RNAs encoded by said gene and related nucleic acids, and (3) methods to identify compounds that bind and/or inhibit said protein(s).

In one embodiment the present invention relates to an isolated nucleic acid molecule encoding FtsY protein.

In another embodiment, the invention relates to a nucleic acid molecule comprising the nucleotide sequence identified as SEQ ID NO:1, SEQ ID NO:3, or SEQ ID NO:4.

In another embodiment, the present invention relates to a nucleic acid that encodes SEQ ID NO:2.

In another embodiment the present invention relates to an isolated protein molecule, wherein said protein molecule comprises the sequence identified as SEQ ID NO:2.

In yet another embodiment, the present invention relates to a recombinant DNA vector that incorporates the FtsY gene in operable linkage to gene expression sequences enabling the gene to be transcribed and translated in a host cell.

In still another embodiment the present invention relates to host cells that have been transformed or transfected with the cloned FtsY gene such that said gene is expressed in the host cell.

This invention also provides a method of determining whether a nucleic acid sequence of the present invention, or fragment thereof, is present in a sample, comprising contacting the sample, under suitable hybridization conditions, with a nucleic acid probe of the present invention.

In a still further embodiment, the present invention relates to a method for identifying compounds that bind and/or inhibit the FtsY protein.

DETAILED DESCRIPTION OF THE INVENTION

"ORF" (i.e. "open reading frame") designates a region of genomic DNA beginning with a Met or other initiation codon and terminating with a translation stop codon, that potentially encodes a protein product. "Partial ORF" means a portion of an ORF as disclosed herein such that the initiation codon, the stop codon, or both are not disclosed.

"Consensus sequence" refers to an amino acid or nucleotide sequence that may suggest the biological function of a protein, DNA, or RNA molecule. Consensus sequences are identified by comparing proteins, RNAs, and gene homologues from different species.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

"Essential genes" or "essential ORFs" or "essential proteins" refer to genomic information or the protein(s) or RNAs encoded thereby, that when disrupted by knockout mutation, or by other mutation, result in a loss of viability of cells harboring said mutation.

"Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation.

"Minimal gene set" refers to a genus comprising about 256 genes conserved among different bacteria such as *M. genitalium* and *H. influenzae*. The minimal gene set may be necessary and sufficient to sustain life. See e.g. A. Mushegian and E. Koonin, "A minimal gene set for cellular life derived by comparison of complete bacterial genomes" *Proc. Nat. Acad. Sci.* 93, 10268–273 (1996).

"Knockout mutant" or "knockout mutation" as used herein refers to an in vitro engineered disruption of a region of native chromosomal DNA, typically within a protein coding region, such that a foreign piece of DNA is inserted within the native sequence. A knockout mutation occurring in a protein coding region prevents expression of the wild-type protein. This usually leads to loss of the function provided by the protein. A "knockout cassette" refers to a fragment of native chromosomal DNA having cloned therein a foreign piece of DNA that may provide a selectable marker.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" applies to all base pairs comprising two single-stranded nucleic acid molecules. "Partially complementary" means one of two single-stranded nucleic acid molecules is shorter than the other, such that one of the molecules remains partially single-stranded.

"Oligonucleotide" refers to a short nucleotide chain comprising from about 2 to about 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which can be used to hybridize with another nucleic acid compound.

The term "hybridization" or "hybridize" as used herein refers to the process by which a single-stranded nucleic acid molecule joins with a complementary strand through nucleotide base pairing.

"Substantially purified" as used herein means a specific isolated nucleic acid or protein, or fragment thereof, in which substantially all contaminants (i.e. substances that differ from said specific molecule) have been separated from said nucleic acid or protein. For example, a protein may, but not necessarily, be "substantially purified" by the IMAC method as described herein.

"Selective hybridization" refers to hybridization under conditions of high stringency. The degree of hybridization between nucleic acid molecules depends upon, for example, the degree of complementarity, the stringency of hybridization, and the length of hybridizing strands.

The term "stringency" relates to nucleic acid hybridization conditions. High stringency conditions disfavor non-homologous base pairing. Low stringency conditions have the opposite effect. Stringency may be altered, for example, by changes in temperature and salt concentration. Typical high stringency conditions comprise hybridizing at 50° C. to 65° C. in 5× SSPE and 50% formamide, and washing at 50° C. to 65° C. in 0.5× SSPE; typical low stringency conditions comprise hybridizing at 35° C. to 37° C. in 5× SSPE and 40% to 45% formamide and washing at 42° C. in 1×–2× SSPE.

"SSPE" denotes a hybridization and wash solution comprising sodium chloride, sodium phosphate, and EDTA, at pH 7.4. A 20× solution of SSPE is made by dissolving 174 g of NaCl, 27.6 g of NaH$_2$PO4.H$_2$O, and 7.4 g of EDTA in 800 ml of H$_2$O. The pH is adjusted with NaOH and the volume brought to 1 liter.

"SSC" denotes a hybridization and wash solution comprising sodium chloride and sodium citrate at pH 7. A 20× solution of SSC is made by dissolving 175 g of NaCl and 88 g of sodium citrate in 800 ml of H$_2$O. The volume is brought to 1 liter after adjusting the pH with 10N NaOH.

The FtsY gene disclosed herein (SEQ ID NO:1) and related nucleic acids (e.g. SEQ ID NO:3 and SEQ ID NO:4) encode an essential integral membrane protein of 70.7 kDa that has an AAA-type ATPase domain at its C-terminus. FtsY participates in targeting proteins to the plasma membrane.

The proteins categorized as "minimal gene set" counterparts are homologous to a set of highly conserved proteins found in other bacteria. The minimal gene set proteins are thought to be essential for viability and are useful targets for the development of new antibacterial compounds.

In one embodiment, the proteins of this invention are purified, and used in a screen to identify compounds that bind and/or inhibit the activity of said proteins. A variety of suitable screens are contemplated for this purpose. For example, the protein(s) can be labeled by known techniques, such as radiolabeling or fluorescent tagging, or by labeling with biotin/avidin. Thereafter, binding of a test compound to a labeled protein can be determined by any suitable means, well known to the skilled artisan.

Skilled artisans will recognize that the DNA molecules of this invention, or fragments thereof, can be generated by general cloning methods. PCR amplification using oligonucleotide primers targeted to any suitable region of SEQ ID NO:1 is preferred. Methods for PCR amplification are widely known in the art. See e.g. *PCR Protocols: A Guide to Method and Application,* Ed. M. Innis et al., Academic Press (1990) or U.S. Pat. No. 4,889,818, which hereby is incorporated by reference. A PCR comprises DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, *Methods in Enzymology,* 68:109–151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., *Oligonucleotide Synthesis, A Practical Approach,* (1984)], or phosphoramidite chemistry.

Protein Production Methods

The present invention relates further to substantially purified proteins encoded by the gene disclosed herein.

Skilled artisans will recognize that proteins can be synthesized by different methods, for example, chemical methods or recombinant methods, as described in U.S. Pat. No. 4,617,149, which hereby is incorporated by reference.

The principles of solid phase chemical synthesis of polypeptides are well known in the art and may be found in general texts relating to this area. See, e.g., H. Dugas and C. Penney, *Bioorganic Chemistry* (1981) Springer-Verlag, New York, 54–92. Peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be made by recombinant DNA methods. Recombinant methods are preferred if a high yield is desired. Recombinant methods involve expressing the cloned gene in a suitable host cell. The gene is introduced into the host cell by any suitable means, well known to those skilled in the art. While chromosomal integration of the cloned gene is within the scope of the present invention, it is preferred that the cloned gene be maintained extra-chromosomally, as part of a vector in which the gene is in operable-linkage to a promoter.

Recombinant methods can also be used to overproduce a membrane-bound or membrane-associated protein. In some cases, membranes prepared from recombinant cells expressing such proteins provide an enriched source of the protein.

Expressing Recombinant Proteins in Procaryotic and Eucaryotic Host Cells

Procaryotes are generally used for cloning DNA sequences and for constructing vectors. For example, the *Escherichia coli* K12 strain 294 (ATCC No. 31446) is particularly useful for expression of foreign proteins. Other strains of *E. coli*, bacilli such as *Bacillus subtilis*, enterobacteriaceae such as *Salmonella typhimurium* or *Serratia marcescans*, various Pseudomonas species may also be employed as host cells in cloning and expressing the recombinant proteins of this invention. Also contemplated are various strains of Streptococcus and Streptocmyces.

For effective recombinant protein production, a gene must be linked to a promoter sequence. Suitable bacterial promoters include b -lactamase [e.g. vector pGX2907, ATCC 39344, contains a replicon and b -lactamase gene], lactose systems [Chang et al., *Nature* (London), 275:615 (1978); Goeddel et al., *Nature* (London), 281:544 (1979)], alkaline phosphatase, and the tryptophan (trp) promoter system [vector pATH1 (ATCC 37695)] designed for the expression of a trpE fusion protein. Hybrid promoters such as the tac promoter (isolatable from plasmid pDR540, ATCC-37282) are also suitable. Promoters for use in bacterial systems also will contain a Shine-Dalgarno sequence, operably linked to the DNA encoding the desired polypeptides. These examples are illustrative rather than limiting.

A variety of mammalian cells and yeasts are also suitable hosts. The yeast *Saccharomyces cerevisiae* is commonly used. Other yeasts, such as *Kluyveromyces lactis*, are also suitable. For expression of recombinant genes in Saccharomyces, the plasmid YRp7 (ATCC-40053), for example, may be used. See, e.g., L. Stinchcomb, et al., *Nature*, 282:39 (1979); J. Kingsman et al., *Gene*, 7:141 (1979); S. Tschemper et al., *Gene*, 10:157 (1980). Plasmid YRp7 contains the TRP1 gene, a selectable marker for a trp1 mutant.

Purification of Recombinantly-Produced Protein

An expression vector carrying a nucleic acid or gene of the present invention is transformed or transfected into a suitable host cell using standard methods. Cells that contain the vector are propagated under conditions suitable for expression of a recombinant protein. For example, if the gene is under the control of an inducible promoter, then suitable growth conditions would incorporate the appropriate inducer. The recombinantly-produced protein may be purified from cellular extracts of transformed cells by any suitable means.

In a preferred process for protein purification a gene is modified at the 5' end, or at some other position, such that the encoded protein incorporates several histidine residues (viz. "histidine tag"). This "histidine tag" enables "immobilized metal ion affinity chromatography" (IMAC), a single-step protein purification method described in U.S. Pat. No. 4,569,794, which hereby is incorporated by reference. The IMAC method enables isolation of substantially pure protein starting from a crude cellular extract.

As skilled artisans will recognize, owing to the degeneracy of the code, the proteins of the invention can be encoded by a large genus of different nucleic acid sequences. This invention further comprises said genus.

The ribonucleic acid compounds of the invention may be prepared using the polynucleotide synthetic methods discussed supra, or they may be prepared enzymatically using RNA polymerase to transcribe a DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of a template. See, J. Sambrook, et al., supra, at 18.82–18.84.

This invention also provides nucleic acids that are complementary to the sequences disclosed herein.

The present invention also provides probes and primers, useful for a variety of molecular biology techniques including, for example, hybridization screens of genomic or subgenomic libraries, or detection and quantification of mRNA species as a means to analyze gene expression. A nucleic acid compound is provided comprising any of the sequences disclosed herein, or a complementary sequence thereof, or a fragment thereof, which is at least 15 base pairs in length, and which will hybridize selectively to *Streptococcus pneumoniae* DNA or mRNA. Preferably, the 15 or more base pair compound is DNA. A probe or primer length of at least 15 base pairs is dictated by theoretical and practical considerations. See e.g. B. Wallace and G. Miyada, "Oligonucleotide Probes for the Screening of Recombinant DNA Libraries," In *Methods in Enzymology*, Vol. 152, 432–442, Academic Press (1987).

The probes and primers of this invention can be prepared by methods well known to those skilled in the art (See e.g. Sambrook et al. supra). In a preferred embodiment the probes and primers are synthesized by the polymerase chain reaction (PCR).

The present invention also relates to recombinant DNA cloning vectors and expression vectors comprising the nucleic acids of the present invention. Preferred nucleic acid vectors are those that comprise DNA. The skilled artisan understands that choosing the most appropriate cloning vector or expression vector depends on the availability of restriction sites, the type of host cell into which the vector is to be transfected or transformed, the purpose of transfection or transformation (e.g., stable transformation as an extrachromosomal element, or integration into a host chromosome), the presence or absence of readily assayable or selectable markers (e.g., antibiotic resistance and metabolic markers of one type and another), and the number of gene copies desired in the host cell.

Suitable vectors comprise RNA viruses, DNA viruses, lytic bacteriophages, lysogenic bacteriophages, stable bacteriophages, plasmids, viroids, and the like. The most preferred vectors are plasmids.

Host cells harboring the nucleic acids disclosed herein are also provided by the present invention. A preferred host is *E. coli* transfected or transformed with a vector comprising a nucleic acid of the present invention.

The invention also provides a host cell capable of expressing a gene described herein, said method comprising transforming or otherwise introducing into a host cell a recombinant DNA vector comprising an isolated DNA sequence that encodes said gene. The preferred host cell is any strain of *E. coli* that can accommodate high level expression of an exogenously introduced gene. Transformed host cells are cultured under conditions well known to skilled artisans, such that said gene is expressed, thereby producing the encoded protein in the recombinant host cell.

To discover compounds having antibacterial activity, one can look for agents that inhibit cell growth and/or viability by, for example, inhibiting enzymes required for cell wall biosynthesis, and/or by identifying agents that interact with membrane proteins. A method for identifying such compounds comprises contacting a suitable protein or membrane preparation with a test compound and monitoring by any suitable means an interaction and/or inhibition of a protein of this invention.

For example, the instant invention provides a screen for compounds that interact with the proteins of the invention, said screen comprising:

a) preparing a FtsY protein, or membranes enriched in said protein;

b) exposing said protein or membranes to a test compound; and c) detecting an interaction of said protein with said compound by any suitable means.

The screening method of this invention may be adapted to automated procedures such as a PANDEX® (Baxter-Dade Diagnostics) system, allowing for efficient high-volume screening of compounds.

In a typical screen, a protein is prepared as described herein, preferably using recombinant DNA technology. A test compound is introduced into a reaction vessel containing said protein. Since the FtsY has been identified as a GTPase, its activity can be detected using $\gamma$-$^{32}$P-GTP as a substrate. (Power and Walter, *Science*, 269, 1422, 1995). The enzymatic activity of said protein in the presence of a substrate, for example, $\gamma$-$^{32}$P-GTP, is monitored by any suitable means.

In another embodiment of a screening protocol FtsY is prepared as described herein, preferably using recombinant DNA technology. A test compound is introduced into a reaction vessel containing the FtsY protein or fragment thereof. Binding of FtsY by a test compound is determined by any suitable means. For example, in one method radioactively- labeled or chemically-labeled test compound may be used. Binding of the protein by the compound is assessed, for example, by quantifying bound label versus unbound label using any suitable method. Binding of a test compound may also be carried out by a method disclosed in U.S. Pat. No. 5,585,277, which hereby is incorporated by reference. In this method, binding of a test compound to a protein is assessed by monitoring the ratio of folded protein to unfolded protein, for example by monitoring sensitivity of said protein to a protease, or amenability to binding of said protein by a specific antibody against the folded state of the protein.

The foregoing screening methods are useful for identifying a ligand of a FtsY protein, perhaps as a lead to a pharmaceutical compound for modulating the state of differentiation of an appropriate tissue. A ligand that binds FtsY, or related fragment thereof, is identified, for example, by combining a test ligand with FtsY under conditions that cause the protein to exist in a ratio of folded to unfolded states. If the test ligand binds the folded state of the protein, the relative amount of folded protein will be higher than in the case of a test ligand that does not bind the protein. The ratio of protein in the folded versus unfolded state is easily determinable by, for example, susceptibility to digestion by a protease, or binding to a specific antibody, or binding to chaperonin protein, or binding to any suitable surface.

The following examples more fully describe the present invention. Those skilled in the art will recognize that the particular reagents, equipment, and procedures described are merely illustrative and are not intended to limit the present invention in any manner.

EXAMPLE 1

Production of a Vector for Expressing *S. pneumoniae* FtsY in a Host Cell

An expression vector suitable for expressing *S. pneumoniae* FtsY in a variety of procaryotic host cells, such as *E. coli*, is easily made. The vector contains an origin of replication (Ori), an ampicillin resistance gene (Amp) useful for selecting cells which have incorporated the vector following a tranformation procedure, and further comprises the T7 promoter and T7 terminator sequences in operable linkage to the FtsY coding region. Plasmid pET11A (obtained from Novogen, Madison, Wis.) is a suitable parent plasmid. pET11A is linearized by restriction with endonucleases NdeI and BamHI. Linearized pET11A is ligated to a DNA fragment bearing NdeI and BamHI sticky ends and comprising the coding region of the *S. pneumoniae* FtsY (SEQ ID NO:1). The coding region for FtsY is easily produced by PCR technology using suitably designed primers to the ends of the coding region specified in SEQ ID NO:1.

The FtsY encoding nucleic acid used in this construct is slightly modified at the 5' end (amino terminus of encoded protein) in order to simplify purification of the encoded protein product. For this purpose, an oligonucleotide encoding 8 histidine residues is inserted after the ATG start codon. Placement of the histidine residues at the amino terminus of the encoded protein serves to enable the IMAC one-step protein purification procedure.

EXAMPLE 2

Recombinant Expression and Purification of a Protein Encoded by *S. pneumoniae* FtsY An expression vector that carries FtsY from the *S. pneumoniae* genome as disclosed herein and which FtsY is operably-linked to an expression promoter is transformed into *E. coli* BL21 (DE3) (hsdS gal 1cIts857 ind1Sam7nin5lacUV5-T7gene 1) using standard methods (see Example 4). Transformants, selected for resistance to ampicillin, are chosen at random and tested for the presence of the vector by agarose gel electrophoresis using quick plasmid preparations. Colonies which contain the vector are grown in L broth and the protein product encoded by the vector-borne ORF is purified by immobilized metal ion affinity chromatography (IMAC), essentially as described in U.S. Pat. No. 4,569,794.

Briefly, the IMAC column is prepared as follows. A metal-free chelating resin (e.g. Sepharose 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract containing the recombinant protein product.

After removing unbound proteins and other materials by washing the column with any suitable buffer, pH 7.5, the bound protein is eluted in any suitable buffer at pH 4.3, or preferably with an imidizole-containing buffer at pH 7.5.

We claim:

1. An isolated nucleic acid compound encoding a protein having the amino acid sequence that is SEQ ID NO:2.

2. An isolated nucleic acid compound, wherein said compound has a sequence selected from the group consisting of:
   (a) SEQ ID NO:1;
   (b) SEQ ID NO:3;
   (c) a nucleic acid compound complementary to (a) or (b).

3. An isolated nucleic acid compound, wherein said compound has the sequence specified as SEQ ID NO:4.

4. An isolated nucleic acid compound of claim 2 wherein the sequence of said compound is SEQ ID NO:1 or a sequence complementary to SEQ ID NO:1.

5. An isolated nucleic acid compound of claim 2 wherein the sequence of said compound is SEQ ID NO:3 or a sequence complementary to SEQ ID NO:3.

6. An isolated nucleic acid compound that hybridizes to SEQ ID NO:1 or SEQ ID NO:3 under low stringency conditions and encodes a FtsY protein.

7. An isolated nucleic acid compound that hybridizes to SEQ ID NO:1 or SEQ ID NO:3 under high stringency conditions.

8. A vector comprising an isolated nucleic acid compound of claim 2.

9. The vector, of claim 8, wherein said isolated nucleic acid compound is SEQ ID NO:1, operably-linked to a promoter sequence.

10. A host cell containing a vector of claim 8.

11. A host cell containing a vector of claim 9.

12. A method for constructing a recombinant host cell having the potential to express SEQ ID NO:2, said method comprising introducing into said host cell a vector of claim 9.

13. A method for expressing SEQ ID NO:2 in a recombinant host cell of claim 12, said method comprising culturing said recombinant host cell under conditions suitable for gene expression.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1278 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..1278

(xi) SEQUENCE DESCRIPTION: SEQ ID NO:1:

```
ATG GGA TTG TTT GAC CGT CTA TTC GGA AAA AAA GAA GAA CCT AAA ATC        48
Met Gly Leu Phe Asp Arg Leu Phe Gly Lys Lys Glu Glu Pro Lys Ile
 1               5                  10                  15

GAA GAA GTT GTA AAA GAA GCT CTG GAA AAT CTT GAT TTG TCT GAA GAT        96
Glu Glu Val Val Lys Glu Ala Leu Glu Asn Leu Asp Leu Ser Glu Asp
                20                  25                  30

GTT GAT CCT ACC TTC ACA GAA GTT GAG GAA GTT TCT CAG GAA GAA GCA       144
Val Asp Pro Thr Phe Thr Glu Val Glu Glu Val Ser Gln Glu Glu Ala
            35                  40                  45

GAG GTT GAA ATT GTT GAA CAA GCT GTG TTC CAA GAA GAG GAA ATC CAA       192
Glu Val Glu Ile Val Glu Gln Ala Val Phe Gln Glu Glu Glu Ile Gln
        50                  55                  60

GAC ACA GTT GAA GAA AGT CTG GAT TTA GAG CCA GTT GTA GAA GTT TCT       240
Asp Thr Val Glu Glu Ser Leu Asp Leu Glu Pro Val Val Glu Val Ser
65                  70                  75                  80

CAA AAA GAA GTC GAA GAA TTT CCA CAC TCA GAA GAA GGG AAT ACT GAG       288
Gln Lys Glu Val Glu Glu Phe Pro His Ser Glu Glu Gly Asn Thr Glu
                85                  90                  95

TTT CTA GAG ACT ATA GAA GAA AAT AAT TCT GAA GTT CTT GAA CCA GAA       336
Phe Leu Glu Thr Ile Glu Glu Asn Asn Ser Glu Val Leu Glu Pro Glu
                100                 105                 110

AGG CCT CAA GCA GAA GAA ACC GTT CAG GAA AAA TAT GAC CGC AGT CTT       384
Arg Pro Gln Ala Glu Glu Thr Val Gln Glu Lys Tyr Asp Arg Ser Leu
            115                 120                 125

AAG AAA ACT CGT ACA GGT TTC GGT GCC CGC TTG AAT GCC TTC TTT GCT       432
Lys Lys Thr Arg Thr Gly Phe Gly Ala Arg Leu Asn Ala Phe Phe Ala
        130                 135                 140

AAC TTC CGC TCT GTT GAC GAA GAA TTT TTC GAG GAA CTG GAA GAA CTG       480
Asn Phe Arg Ser Val Asp Glu Glu Phe Phe Glu Glu Leu Glu Glu Leu
145                 150                 155                 160

CTG ATT ATG AGT GAT GTT GGT GTC CAA GTC GCT TCT AAC TTA ACG GAG       528
Leu Ile Met Ser Asp Val Gly Val Gln Val Ala Ser Asn Leu Thr Glu
```

-continued

```
                        165                 170                 175
GAA CTA CGT TAC GAA GCC AAG CTT GAA AAT GCC AAG AAA CCT GAT GCA      576
Glu Leu Arg Tyr Glu Ala Lys Leu Glu Asn Ala Lys Lys Pro Asp Ala
                180                 185                 190

CTT CGT CGT GTC ATC ATT GAG AAA TTG GTT GAG CTT TAT GAA AAG GAT      624
Leu Arg Arg Val Ile Ile Glu Lys Leu Val Glu Leu Tyr Glu Lys Asp
            195                 200                 205

GGT AGC TAC GAT GAA AGC ATC CAC TTC CAA GAT AAC TTG ACA GTT ATG      672
Gly Ser Tyr Asp Glu Ser Ile His Phe Gln Asp Asn Leu Thr Val Met
        210                 215                 220

CTC TTT GTT GGT GTG AAT GGT GTT GGG AAA ACA ACT TCT ATC GGA AAA      720
Leu Phe Val Gly Val Asn Gly Val Gly Lys Thr Thr Ser Ile Gly Lys
225                 230                 235                 240

CTA GCC CAC CGC TAC AAA CAA GCT GGT AAG AAG GTC ATG CTG GTT GCA      768
Leu Ala His Arg Tyr Lys Gln Ala Gly Lys Lys Val Met Leu Val Ala
                245                 250                 255

GCA GAT ACC TTC CGT GCG GGT GCA GTA GCT CAG CTA GCT GAA TGG GGC      816
Ala Asp Thr Phe Arg Ala Gly Ala Val Ala Gln Leu Ala Glu Trp Gly
            260                 265                 270

CGA CGA GTA GAT GTT CCA GTA GTA ACT GGA CCT GAA AAA GCT GAT CCA      864
Arg Arg Val Asp Val Pro Val Val Thr Gly Pro Glu Lys Ala Asp Pro
        275                 280                 285

GCC AGC GTG GTC TTT GAT GGT ATG GAA CGT GCC GTG GCT GAA GGT ATC      912
Ala Ser Val Val Phe Asp Gly Met Glu Arg Ala Val Ala Glu Gly Ile
    290                 295                 300

GAT ATT CTC ATG ATT GAT ACT GCT GGT CGT CTG CAA AAT AAG GAT AAC      960
Asp Ile Leu Met Ile Asp Thr Ala Gly Arg Leu Gln Asn Lys Asp Asn
305                 310                 315                 320

CTT ATG GCT GAG TTG GAA AAG ATT GGT CGT ATT ATC AAA CGT GTT GTG     1008
Leu Met Ala Glu Leu Glu Lys Ile Gly Arg Ile Ile Lys Arg Val Val
                325                 330                 335

CCA GAA GCA CCA CAT GAA ACC TTC TTG GCA CTT GAT GCA TCA ACA GGT     1056
Pro Glu Ala Pro His Glu Thr Phe Leu Ala Leu Asp Ala Ser Thr Gly
            340                 345                 350

CAA AAT GCC CTA GTA CAG GCC AAA GAA TTT TCG AAA ATC ACA CCT TTA     1104
Gln Asn Ala Leu Val Gln Ala Lys Glu Phe Ser Lys Ile Thr Pro Leu
        355                 360                 365

ACG GGA ATT GTT TTG ACT AAG ATT GAT GGA ACT GCT CGA GGA GGT GTG     1152
Thr Gly Ile Val Leu Thr Lys Ile Asp Gly Thr Ala Arg Gly Gly Val
    370                 375                 380

GTT CTA GCC ATT CGT GAA GAA CTC AAT ATT CCT GTA AAA TTG ATT GGT     1200
Val Leu Ala Ile Arg Glu Glu Leu Asn Ile Pro Val Lys Leu Ile Gly
385                 390                 395                 400

TTT GGT GAA AAA ATC GAT GAT ATT GGA GAG TTT AAC TCA GAA AAC TTT     1248
Phe Gly Glu Lys Ile Asp Asp Ile Gly Glu Phe Asn Ser Glu Asn Phe
                405                 410                 415

ATG AAA GGT CTC TTG GAA GGT TTA ATC TAA                             1278
Met Lys Gly Leu Leu Glu Gly Leu Ile *
            420                 425
```

(2) INFORMATION FOR SEQ ID NO:2:

(i) SEQUENCE CHARACTERISTICS:
        (A) LENGTH: 425 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Leu Phe Asp Arg Leu Phe Gly Lys Lys Glu Glu Pro Lys Ile
1               5                   10                  15
```

```
Glu Glu Val Val Lys Glu Ala Leu Glu Asn Leu Asp Leu Ser Glu Asp
            20                  25                  30

Val Asp Pro Thr Phe Thr Glu Val Glu Val Ser Gln Glu Glu Ala
        35                  40                  45

Glu Val Glu Ile Val Glu Gln Ala Val Phe Gln Glu Glu Ile Gln
    50                  55                  60

Asp Thr Val Glu Glu Ser Leu Asp Leu Glu Pro Val Val Glu Val Ser
 65              70                  75                  80

Gln Lys Glu Val Glu Glu Phe Pro His Ser Glu Glu Gly Asn Thr Glu
                85                  90                  95

Phe Leu Glu Thr Ile Glu Glu Asn Asn Ser Glu Val Leu Glu Pro Glu
                100                 105                 110

Arg Pro Gln Ala Glu Glu Thr Val Gln Glu Lys Tyr Asp Arg Ser Leu
            115                 120                 125

Lys Lys Thr Arg Thr Gly Phe Gly Ala Arg Leu Asn Ala Phe Phe Ala
    130                 135                 140

Asn Phe Arg Ser Val Asp Glu Phe Phe Glu Glu Leu Glu Glu Leu
145                 150                 155                 160

Leu Ile Met Ser Asp Val Gly Val Gln Val Ala Ser Asn Leu Thr Glu
                165                 170                 175

Glu Leu Arg Tyr Glu Ala Lys Leu Glu Asn Ala Lys Lys Pro Asp Ala
                180                 185                 190

Leu Arg Arg Val Ile Ile Glu Lys Leu Val Glu Leu Tyr Glu Lys Asp
                195                 200                 205

Gly Ser Tyr Asp Glu Ser Ile His Phe Gln Asp Asn Leu Thr Val Met
            210                 215                 220

Leu Phe Val Gly Val Asn Gly Val Gly Lys Thr Thr Ser Ile Gly Lys
225                 230                 235                 240

Leu Ala His Arg Tyr Lys Gln Ala Gly Lys Lys Val Met Leu Val Ala
                245                 250                 255

Ala Asp Thr Phe Arg Ala Gly Ala Val Ala Gln Leu Ala Glu Trp Gly
                260                 265                 270

Arg Arg Val Asp Val Pro Val Val Thr Gly Pro Glu Lys Ala Asp Pro
            275                 280                 285

Ala Ser Val Val Phe Asp Gly Met Glu Arg Ala Val Ala Glu Gly Ile
            290                 295                 300

Asp Ile Leu Met Ile Asp Thr Ala Gly Arg Leu Gln Asn Lys Asp Asn
305                 310                 315                 320

Leu Met Ala Glu Leu Glu Lys Ile Gly Arg Ile Ile Lys Arg Val Val
                325                 330                 335

Pro Glu Ala Pro His Glu Thr Phe Leu Ala Leu Asp Ala Ser Thr Gly
            340                 345                 350

Gln Asn Ala Leu Val Gln Ala Lys Glu Phe Ser Lys Ile Thr Pro Leu
            355                 360                 365

Thr Gly Ile Val Leu Thr Lys Ile Asp Gly Thr Ala Arg Gly Gly Val
    370                 375                 380

Val Leu Ala Ile Arg Glu Glu Leu Asn Ile Pro Val Lys Leu Ile Gly
385                 390                 395                 400

Phe Gly Glu Lys Ile Asp Asp Ile Gly Glu Phe Asn Ser Glu Asn Phe
                405                 410                 415

Met Lys Gly Leu Leu Glu Gly Leu Ile
                420                 425
```

(2) INFORMATION FOR SEQ ID NO:3:

(i) SEQUENCE CHARACTERISTICS:
        (A) LENGTH: 1278 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

```
AUGGGAUUGU UUGACCGUCU AUUCGGAAAA AAGAAGAAC CUAAAAUCGA AGAAGUUGUA      60
AAAGAAGCUC UGGAAAAUCU UGAUUUGUCU GAAGAUGUUG AUCCUACCUU CACAGAAGUU    120
GAGGAAGUUU CUCAGGAAGA AGCAGAGGUU GAAAUUGUUG AACAAGCUGU GUUCCAAGAA    180
GAGGAAAUCC AAGACACAGU UGAAGAAAGU CUGGAUUUAG AGCCAGUUGU AGAAGUUUCU    240
CAAAAGAAG UCGAAGAAUU UCCACACUCA GAAGAAGGGA AUACUGAGUU UCUAGAGACU     300
AUAGAAGAAA AUAAUUCUGA AGUUCUUGAA CCAGAAAGGC CUCAAGCAGA AGAAACCGUU    360
CAGGAAAAAU AUGACCGCAG UCUUAAGAAA ACUCGUACAG GUUUCGGUGC CCGCUUGAAU    420
GCCUUCUUUG CUAACUUCCG CUCUGUUGAC GAAGAAUUUU UCGAGGAACU GGAAGAACUG    480
CUGAUUAUGA GUGAUGUUGG UGUCCAAGUC GCUUCUAACU UAACGGAGGA ACUACGUUAC    540
GAAGCCAAGC UUGAAAAUGC CAAGAAACCU GAUGCACUUC GUCGUGUCAU CAUUGAGAAA    600
UUGGUUGAGC UUUAUGAAAA GGAUGGUAGC UACGAUGAAA GCAUCCACUU CCAAGAUAAC    660
UUGACAGUUA UGCUCUUUGU UGGUGUGAAU GGUGUUGGGA AACAACUUC UAUCGGAAAA     720
CUAGCCCACC GCUACAAACA AGCUGGUAAG AAGGUCAUGC UGGUUGCAGC AGAUACCUUC    780
CGUGCGGGUG CAGUAGCUCA GCUAGCUGAA UGGGGCCGAC GAGUAGAUGU UCCAGUAGUA    840
ACUGGACCUG AAAAAGCUGA UCCAGCCAGC GUGGUCUUUG AUGGUAUGGA ACGUGCCGUG    900
GCUGAAGGUA UCGAUAUUCU CAUGAUUGAU ACUGCUGGUC GUCUGCAAAA UAAGGAUAAC    960
CUUAUGGCUG AGUUGGAAAA GAUUGGUCGU AUUAUCAAAC GUGUUGUGCC AGAAGCACCA   1020
CAUGAAACCU UCUUGGCACU UGAUGCAUCA ACAGGUCAAA AUGCCCUAGU ACAGGCCAAA   1080
GAAUUUCGA AAAUCACACC UUUAACGGGA AUUGUUUUGA CUAAGAUUGA UGGAACUGCU    1140
CGAGGAGGUG UGGUUCUAGC CAUUCGUGAA GAACUCAAUA UUCCUGUAAA AUUGAUUGGU   1200
UUUGGUGAAA AAAUCGAUGA UAUUGGAGAG UUUAACUCAG AAAACUUUAU GAAAGGUCUC   1260
UUGGAAGGUU UAAUCUAA                                                 1278
```

(2) INFORMATION FOR SEQ ID NO:4:

(i) SEQUENCE CHARACTERISTICS:
        (A) LENGTH: 2764 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
AGAACCCTTG GATGCAGCCA TTCAGAAGAT TTCTCCAGAA TTGTTTGACC AATATGAAAT     60
CTTTAAATCA CGTGAAATGT TGCTAGAATG GTCACCAAAG AATGTTCATA AGCAACAGG    120
```

```
TTTGGCAAAA CTAATCAGCC ATCTTGGAAT CGACCAAAGT CAAGTGATGG CTTGTGGTGA    180

CGAGGCCAAT GACCTCTCTA TGATTGAATG GGCAGGTCTT GGTGTTGCTA TGCAAAACGC    240

TGTTCCTGAA GTAAAGGCAG CCGCAAATGT AGTGACGCCG ATGACCAACG ATGAGGAAGC    300

TGTCGCCTGG GCTATCGAAG AATATGTGCT AAAGGAGAAC TAAGATATGG GATTGTTTGA    360

CCGTCTATTC GGAAAAAAAG AAGAACCTAA AATCGAAGAA GTTGTAAAAG AAGCTCTGGA    420

AAATCTTGAT TTGTCTGAAG ATGTTGATCC TACCTTCACA GAAGTTGAGG AAGTTTCTCA    480

GGAAGAAGCA GAGGTTGAAA TTGTTGAACA AGCTGTGTTC CAAGAAGAGG AAATCCAAGA    540

CACAGTTGAA GAAAGTCTGG ATTTAGAGCC AGTTGTAGAA GTTTCTCAAA AGAAGTCGA    600

AGAATTTCCA CACTCAGAAG AAGGGAATAC TGAGTTTCTA GAGACTATAG AAGAAAATAA    660

TTCTGAAGTT CTTGAACCAG AAAGGCCTCA AGCAGAAGAA ACCGTTCAGG AAAAATATGA    720

CCGCAGTCTT AAGAAAACTC GTACAGGTTT CGGTGCCCGC TTGAATGCCT TCTTTGCTAA    780

CTTCCGCTCT GTTGACGAAG AATTTTTCGA GGAACTGGAA GAACTGCTGA TTATGAGTGA    840

TGTTGGTGTC CAAGTCGCTT CTAACTTAAC GGAGGAACTA CGTTACGAAG CCAAGCTTGA    900

AAATGCCAAG AAACCTGATG CACTTCGTCG TGTCATCATT GAGAAATTGG TTGAGCTTTA    960

TGAAAAGGAT GGTAGCTACG ATGAAAGCAT CCACTTCCAA GATAACTTGA CAGTTATGCT   1020

CTTTGTTGGT GTGAATGGTG TTGGGAAAAC AACTTCTATC GGAAAACTAG CCCACCGCTA   1080

CAAACAAGCT GGTAAGAAGG TCATGCTGGT TGCAGCAGAT ACCTTCCGTG CGGGTGCAGT   1140

AGCTCAGCTA GCTGAATGGG GCCGACGAGT AGATGTTCCA GTAGTAACTG GACCTGAAAA   1200

AGCTGATCCA GCCAGCGTGG TCTTTGATGG TATGGAACGT GCCGTGGCTG AAGGTATCGA   1260

TATTCTCATG ATTGATACTG CTGGTCGTCT GCAAAATAAG GATAACCTTA TGGCTGAGTT   1320

GGAAAAGATT GGTCGTATTA TCAAACGTGT TGTGCCAGAA GCACCACATG AAACCTTCTT   1380

GGCACTTGAT GCATCAACAG GTCAAAATGC CCTAGTACAG GCCAAAGAAT TTTCGAAAAT   1440

CACACCTTTA ACGGGAATTG TTTTGACTAA GATTGATGGA ACTGCTCGAG GAGGTGTGGT   1500

TCTAGCCATT CGTGAAGAAC TCAATATTCC TGTAAAATTG ATTGGTTTTG GTGAAAAAAT   1560

CGATGATATT GGAGAGTTTA ACTCAGAAAA CTTTATGAAA GGTCTCTTGG AAGGTTTAAT   1620

CTAATCAGAA GCAAAAATCC TGCAAGGCAT AAACTTGCAG GAAATTTTTT TATTCTAAGC   1680

GACCATCTTG ACGATAGGTG ATATCTGGTT GCCAAGTCCA TTTGGCACCG AATTTTTCAA   1740

GTAGGTCAAA GCTGGCTTGA GGTCCCATGC TTCCAGCTTT ATAGTCATGA AGTGGGGCAC   1800

CATTTTCAGC CCAGAGCTTT TCAATACGGT CAATCAACTT CCATGACGCA CAAACTTCAT   1860

CCCAGTGGCT AAAGTTAGTT GAGTTGTTAT TTAGGACATC ATAAATCAAT TTTTCGTATG   1920

GTTCTGGAGA AGCACCAGTT GCAGTCGCAT CTGTACGGTA ATCAAGTGAG TTAGGAGCCA   1980

AGTTAAATTC TTCTCCTACT TGCTTCCCAT TTAGGCTAAG AGAGAAGCCT TCTGTTGGTT   2040

GAATATAGAT GGTCAAAATA TTTGGAGCAA GTGGTTCTCC AAAGATAGAA TCCATTTGTT   2100

TAAAGACGAT GTTGACATGA GTTCCTTTTT CAGTCAGTCG TTTACCTGTA CGGAAAAAGA   2160

AAGGAACACC ACGGAATCGA TCGCTGTCTA CAAAGAAGGC ACCAGATGTA AAGGTTTCAG   2220

TTGTTGATTC TGGATTCACA TTTGGCTCGC TACGATAAGA GATGTATTTC ATGCCATCAA   2280

TCTTACCAGA GCGGTATTGC CCACGGATAA AGTGTTCTTT GAGTTCTTCA TCAGTTGGAT   2340

GATAGAGGTT TTTAAAGACC TTAATCTTTT CAGCACGAAT CTCGTCTTTT GTGAAGCTTG   2400

CTGGTTTGTC CATGGCGAGG AGCGAAAGAA GTTGTAGAGT GTGGTTTTGG ACCATGTCAC   2460

GGAGGGCACC GGATTGGTCA TAGTAGCCAC CACGTTCTTC TACACCCAAG CTCCGCAAAG   2520
```

-continued

```
GTAATTTGAA CATTGTCGAA AAATCCTTGT TCCAAACGTT TTCAAAAATC AAGTTTGCAA    2580

AGCGAACTGC AAAGATGCTT TGGATCATTT CCTTACCAAG ATAATGGTCG ATACGGAAAA    2640

TTTGTTCTTC GTCAAATGTT GCTAGGAGTT CGTCATTCAA CTTGTTTGCA GTTGCGTAAT    2700

CTGTACCAAA TGGTTTTTCA ACGATCAAGC GCTCAAAACC TTTGCCATCG ACTCTAGAGG    2760

ATCC                                                                 2764
```